US012746093B2

(12) United States Patent
Witkow

(10) Patent No.: US 12,746,093 B2
(45) Date of Patent: Sep. 29, 2026

(54) SURGICAL SPECIMEN MAPPING MECHANISM

(71) Applicant: Emet Surgical Inc., Aurora, CO (US)

(72) Inventor: Robert Witkow, Denver, CO (US)

(73) Assignee: Emet Surgical Inc., Aurora, CO (US)

( * ) Notice: Subject to any disclaimer, the term of this patent is extended or adjusted under 35 U.S.C. 154(b) by 219 days.

(21) Appl. No.: 18/630,111

(22) Filed: Apr. 9, 2024

(65) Prior Publication Data

US 2024/0341909 A1 Oct. 17, 2024

Related U.S. Application Data

(60) Provisional application No. 63/496,133, filed on Apr. 14, 2023.

(51) Int. Cl.
*A61B 90/00* (2016.01)

(52) U.S. Cl.
CPC ...... *A61B 90/39* (2016.02); *A61B 2090/3991* (2016.02)

(58) Field of Classification Search
CPC ............ A61B 90/39; A61B 2090/3991; A61B 2090/3908; A61B 2090/395
See application file for complete search history.

(56) References Cited

U.S. PATENT DOCUMENTS

| | | | | |
|---|---|---|---|---|
| 7,988,618 | B2 * | 8/2011 | Mikkaichi | A61B 1/00154 600/114 |
| 10,111,727 | B2 * | 10/2018 | Opperman | A61B 90/39 |
| 11,464,599 | B1 | 10/2022 | Opperman et al. | |
| D990,679 | S | 6/2023 | Opperman | |
| 2005/0277871 | A1 * | 12/2005 | Selis | A61B 90/98 600/564 |
| 2006/0229529 | A1 * | 10/2006 | Wright | A61B 90/92 600/567 |
| 2007/0157937 | A1 * | 7/2007 | Mikkaichi | A61B 90/39 128/898 |
| 2016/0331485 | A1 * | 11/2016 | Opperman | A61B 90/39 |
| 2022/0401180 | A1 * | 12/2022 | Opperman | A61B 90/98 |
| 2023/0310113 | A1 | 10/2023 | Opperman | |
| 2024/0008860 | A1 * | 1/2024 | Phillips | A61B 90/39 |

* cited by examiner

*Primary Examiner* — Jonathan T Kuo
(74) *Attorney, Agent, or Firm* — The Roy Gross Law Firm, LLC; Roy D. Gross

(57) ABSTRACT

According to one embodiment, a marking system is disclosed. The marking system includes a specimen marker to be inserted within mass tissue and a first set of specimen markers be inserted within the mass tissue to provide a mapping for removing the mass tissue.

5 Claims, 6 Drawing Sheets

SURGICAL SPECIMEN MAPPING MECHANISM

CROSS-REFERENCE

This patent application is related to and, under 35 U.S.C. 119, claims the benefit of and priority to U.S. Provisional Patent Application No. 63/496,133 filed Apr. 14, 2023, which is hereby incorporated herein by reference.

FIELD OF THE INVENTION

The present invention relates to medical devices, more particularly, surgical specimen margin orientation marking.

BACKGROUND

Surgical specimen margin orientation marking for endoscopic, robotic, laparoscopic, or other surgery types where body tissue is removed, is critical for pathological diagnosis, tumor excision and other margin marking.

BRIEF DESCRIPTION OF THE DRAWINGS

The present invention will be understood more fully from the detailed description given below and from the accompanying drawings of various embodiments of the invention. The drawings, however, should not be taken to limit the invention to the specific embodiments, but are for explanation and understanding only.

DETAILED DESCRIPTION

An example of surgical specimen margin orientation marking may be featured in an endoscopic excision of a tumor. In such an example, the tumor is removed and forwarded to a pathologist for evaluation by frozen section or permanent wax-based pathology. The pathologist subsequently performs an analysis to identify malignancy at one or more of the tumor margins. The pathologist may direct the surgeon of additional tissue needing to be excised, the orientation and location of which is critical for proper and accurate excision.

Figure 1A:
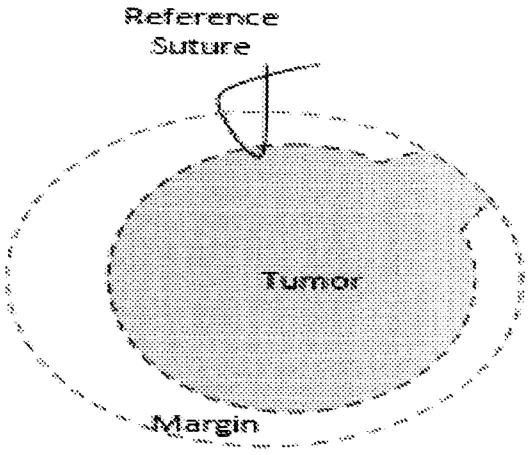
FIGS. 1A & 1B illustrate a conventional surgical specimen margin orientation marking system.

Surgical specimen margin orientation marking typically involves ink marking (e.g., ex-vivo marking) once a specimen has been removed. FIG. 1A illustrates one embodiment of a conventional marking technique in which a specimen mass (or tumor) is marked with a dotted line to differentiate the mass from surrounding tissue (or margin). As shown in FIG. 1A, a reference suture is added at a particular position, such as "12:00 o'clock", on the mass. As defined herein, ex-vivo marking refers to marking that occurs outside of the body, while in-vivo marking refers to marking that occurs inside of the body.

Figure 1B:
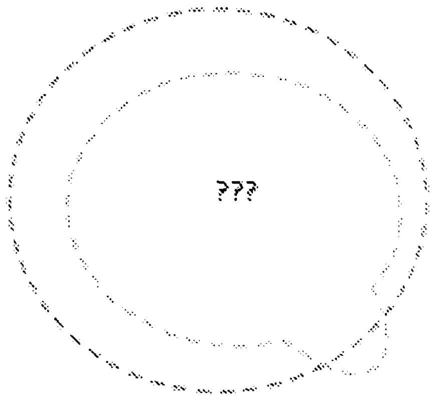

The specimen is subsequently delivered to a pathologist, who after examination, communicates to the surgeon locations at which additional tissue is to be removed. However, this approach is inaccurate and subject to error because the technique has no corresponding in-vivo marking, and particularly in instances in which the suture is accidentally removed or the orientation of the specimen is changed (e.g., due to being dropped, manipulated, etc.). For example, the surgeon, staff, or pathologist examining the mass may mistakenly manipulate the removed mass. Even in instances in which the suture has not been removed, there may be miscommunication between surgeons and pathologists related to orientation. As a result, it may be difficult for a surgeon to correctly identify the exact location where additional tissue must be removed, as shown in FIG. 1B.

According to one embodiment, a surgical specimen margin orientation marking mechanism is disclosed that comprises a plurality of surgical specimen margin markers (or specimen markers) configured to provide a mapping between a tumor mass and surrounding tissue. Reference in the specification to "one embodiment" or "an embodiment" means that a particular feature, structure, or characteristic described in connection with the embodiment is included in at least one embodiment of the invention. The appearances of the phrase "in one embodiment" in various places in the specification are not necessarily all referring to the same embodiment.

In the following description, numerous details are set forth. It will be apparent, however, to one skilled in the art, that the present invention may be practiced without these specific details. In other instances, well-known structures and devices are shown in block diagram form, rather than in detail, in order to avoid obscuring the present invention.

Figure 2:
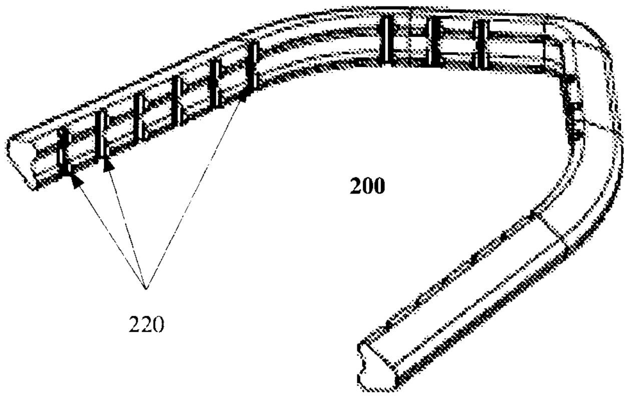
FIG. 2 illustrates one embodiment of surgical specimen margin marker.

FIG. 2 illustrates one embodiment of a surgical specimen margin markers comprising a marking clip 200. Marking clip 200 is placed on tissue to identify one or more locations at which tissue is to be removed. In one embodiment, marking clip 200 includes a plurality of ridge and valleys 220 that enable a non-slip grip on a variety of tissue types (e.g., fatty, fibrous, skin, etc.) implemented to attach to the tissue. In a further embodiment, clip 200 comprises titanium ligature clips. However other embodiments may feature clips 200 constructed of different materials having different shapes and weights.

Figure 3A:
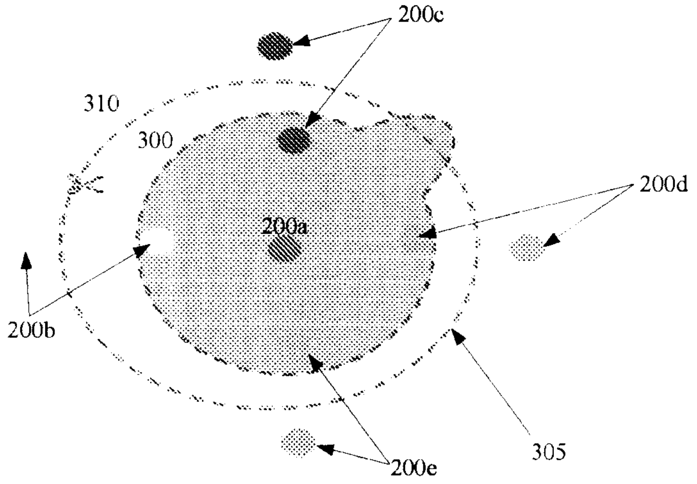
FIGS. 3A & 3B illustrate embodiments of a mass identified by a mapping of surgical specimen margin markers.
Figure 3B:
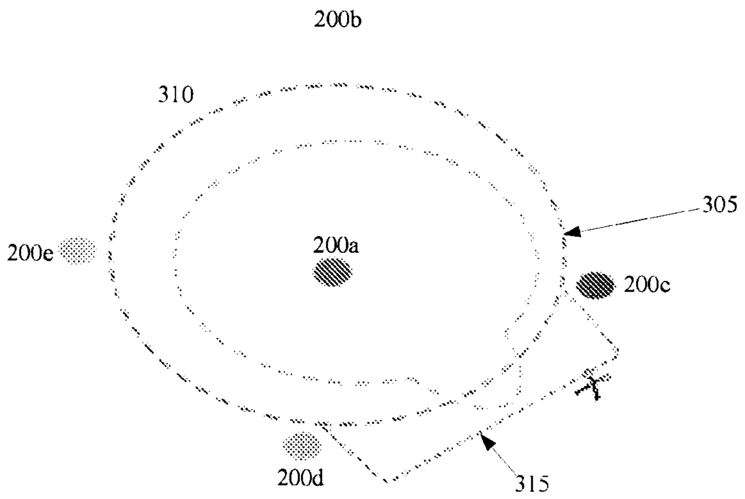

According to one embodiment, each clip 200 is color coded to assist in identifying a position of a mass and surrounding tissue. In such an embodiment, color-coded clips 200 are implemented in pairs to provide a mapping that aligns positions between the mass and the surrounding tissue. FIGS. 3A & 3B illustrate embodiments of a mass 300 and surrounding tissue 310 identified by a mapping of marking clips 200. As shown in FIG. 3A, a mass 300 to be excised is identified by dotted line 305 to differentiate from surrounding tissue 310. In one embodiment, marking clips 200 are placed at a plurality of locations of mass 300 and surrounding tissue 310. In this embodiment, a central marking clip 200*a* is included to identify a midpoint (or midline) of mass 300.

According to one embodiment, clip pairs 200*b*, 200*c*, 200*d* and 200*e* are placed at locations around clip 200*a* within mass 300 and surrounding tissue 310. For example, a single clip of 200*b*, 200*c*, 200*d* and 200*e* is placed within mass 300 at locations around (e.g., 360 degrees) clip 200*a*. Additionally, a second set of clip pairs 200*b*, 200*c*, 200*d* and 200*e* is placed at corresponding locations of surrounding tissue 310. For example, a clip 200*b* is placed in surrounding tissue 310 at a location adjacent to the location of the clip 200*b* located within mass 300. Further, a clip 200*c* is placed in surrounding tissue 310 at a location adjacent to the location of the clip 200*c* located within mass 300, and so forth with clips 200*d* and 200*e*.

In one embodiment, central clip 200*a* and clip pairs 200*b*, 200*c*, 200*d* and 200*e* may be comprised of different colors. For instance, clip 200*a* comprises a first color (e.g., red), while clips 200*b*, 200*c*, 200*d* and 200*e* comprise second (e.g., yellow), third (e.g., purple), fourth (e.g., green) and fifth (e.g., orange) colors, respectively. However, other embodiments may feature different color-coding schemes.

According to one embodiment, a surgeon may excise mass 300 along dotted line 305 to be forwarded for pathological examination. Once mass 300 has been removed, 200*b*, 200*c*, 200*d* and 200*e* remain inserted in the surrounding tissue while mass 300 is examined. In a further embodiment clips 200*b*, 200*c*, 200*d* and 200*e* within the mass 300 are used during examination to provide references. In such an embodiment, the examination of mass 300 may indicate that there is additional tumorous tissue extending into the surrounding tissue 310. Accordingly, examination instructions may be provided with reference to the clips 200. For example, instructions may be provided to remove a portion of additional surrounding tissue 310 between clips 200*c* and 200*d*. Subsequently, the surgeon uses clips 200*c* and 200*d* as references to remove the additional surrounding tissue 310 along dotted line 315, as shown in FIG. 3B.

Figure 4:
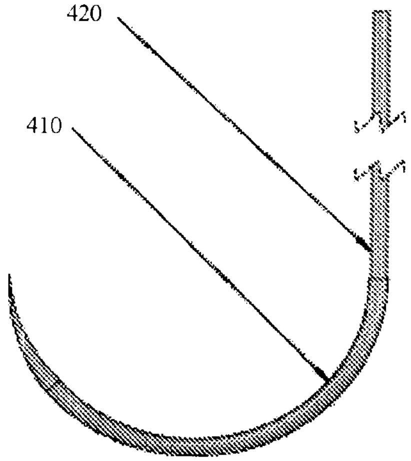
FIG. 4 illustrate another embodiment of surgical specimen margin marker.

In other embodiments, different types of specimen markers may be implemented. One such embodiment is shown in FIG. 4, which illustrates a specimen marker comprising a needle 410 coupled to a suture 420. In this embodiment, the specimen marker comprises a needle 410 coupled to a suture 420. Similar to the marking clip embodiment discussed above, a central needle 410/suture 420 is implemented along with needle 410/suture 420 pairs. In such an embodiment, the central suture 420 and each suture 420 pair comprises a different color (e.g., red, yellow, purple, green and orange) as discussed above with reference to FIG. 3A.

The above-described embodiments, provides a plurality of reference points at locations within a tumor mass, as well as matching points in surrounding tissue to create a mapping that enables precise communications between a surgeon and pathologist.

Whereas many alterations and modifications of the present invention will no doubt become apparent to a person of ordinary skill in the art after having read the foregoing description, it is to be understood that any particular embodiment shown and described by way of illustration is in no way intended to be considered limiting. Therefore, references to details of various embodiments are not intended to limit the scope of the claims, which in themselves recite only those features regarded as the invention.

What is claimed is:

1. A surgical specimen margin orientation marking mechanism comprises a plurality of surgical specimen margin markers configured to provide a mapping between a tumor mass and surrounding tissue, wherein each surgical specimen margin marker comprising a marking clip without sutures placed on tissue to identify one or more locations at which tissue is to be removed or surrounding tissue.

2. A mechanism according to claim 1 wherein one or more of said marking clips including a plurality of ridge and valleys enabling a non-slip grip on a variety of tissue types.

3. A mechanism according to claim 1 wherein one or more of said marking clips comprise titanium ligature clips.

4. A mechanism according to claim 1 wherein one or more of said marking clips being color coded.

5. A method of marking a tumor mass and surrounding tissue comprising: positioning a central marking clip to identify a midpoint of said mass; positioning a first set of clips within said mass at locations around said central marking clip, and positioning a second set of clips at corresponding locations of surrounding tissue.

* * * * *